United States Patent
Bockholt et al.

(10) Patent No.: US 10,584,136 B2
(45) Date of Patent: Mar. 10, 2020

(54) PROCESS FOR SEPARATING ALUMINUM CHLORIDE FROM SILANES

(71) Applicant: Wacker Chemie AG, Munich (DE)

(72) Inventors: Andreas Bockholt, Munich (DE); Konrad Mautner, Burghausen (DE)

(73) Assignee: WACKER CHEMIE AG, Munich (DE)

(*) Notice: Subject to any disclaimer, the term of this patent is extended or adjusted under 35 U.S.C. 154(b) by 168 days.

(21) Appl. No.: 15/576,163

(22) PCT Filed: Apr. 3, 2017

(86) PCT No.: PCT/EP2017/057883
§ 371 (c)(1),
(2) Date: Nov. 21, 2017

(87) PCT Pub. No.: WO2017/178268
PCT Pub. Date: Oct. 19, 2017

(65) Prior Publication Data
US 2018/0170950 A1    Jun. 21, 2018

(30) Foreign Application Priority Data
Apr. 12, 2016 (DE) .................. 10 2016 206 090

(51) Int. Cl.
*C01F 7/20* (2006.01)
*C01B 33/107* (2006.01)
*C07F 7/20* (2006.01)

(52) U.S. Cl.
CPC .......... *C07F 7/20* (2013.01); *C01B 33/10778* (2013.01); *C01P 2006/80* (2013.01)

(58) Field of Classification Search
CPC ........................... C01B 33/10778; C07F 7/20
See application file for complete search history.

(56) References Cited

U.S. PATENT DOCUMENTS

| | | |
|---|---|---|
| 3,475,139 A | 10/1969 | Schwarz et al. |
| 4,224,040 A | 9/1980 | Gazzarrini et al. |
| 2004/0073035 A1* | 4/2004 | Maase .................... C07C 45/50 546/187 |
| 2008/0083606 A1 | 4/2008 | Volland et al. |
| 2010/0266489 A1 | 10/2010 | Rauleder et al. |
| 2015/0290558 A1 | 10/2015 | Mohsseni et al. |
| 2015/0291920 A1 | 10/2015 | Mohsseni et al. |

FOREIGN PATENT DOCUMENTS

| | | |
|---|---|---|
| DE | 1567469 | 8/1970 |
| DE | 2852598 A1 | 6/1979 |
| DE | 10157198 A1 | 5/2002 |
| DE | 102007002536 A1 | 7/2008 |
| DE | 102009027729 A1 | 1/2011 |
| EP | 2930178 A1 | 10/2015 |
| EP | 2930232 A1 | 10/2015 |
| JP | 2005515258 A | 5/2005 |
| WO | 2009049944 A1 | 4/2009 |

* cited by examiner

*Primary Examiner* — Ngoc-Yen Nguyen
(74) *Attorney, Agent, or Firm* — Brooks Kushman P.C.

(57) ABSTRACT

Aluminum chloride is separated from a silane mixture containing aluminum chloride by reacting the aluminum chloride with a compound reactive therewith which forms an ionic liquid or solid, and separating the ionic liquid or solid from the now-purified silane.

19 Claims, No Drawings

PROCESS FOR SEPARATING ALUMINUM CHLORIDE FROM SILANES

CROSS REFERENCE TO RELATED APPLICATIONS

This application is the U.S. National Phase of PCT Appln. No. PCT/EP2017/057883 filed Apr. 3, 2017, which claims priority to German Application No. 10 2016 206 090.2 filed Apr. 12, 2016, the disclosures of which are incorporated in their entirety by reference herein.

BACKGROUND OF THE INVENTION

1. Field of the Invention

The invention relates to a process for separating aluminum chloride from silane liquid by formation of an ionic liquid composed of aluminum chloride with a nitrogen or phosphorus compound.

2. Description of the Related Art

The silane mixture produced in the Müller-Rochow process is referred to as crude silane. It contains a certain amount of aluminum compounds which interfere in the further work-up process and lead to undesirable deposits and subsequent reactions in the plants. It has been said hitherto (CS 147515) that aluminum chloride can be scavenged by reaction with sodium chloride. However, this reaction is sufficiently fast only in the gas phase at high temperatures and is unsuitable for a high mass throughput. The concentration of aluminum compounds in silanes can also be reduced by means of polymers having amine groups (DE 102009027729 A1), vinylpyridine copolymers (DE 2852598), polymer resins without functional groups, e.g. Amberlyte XAD-4®, or clay minerals such as montmorillonite K 10 ™ (WO 2009049944 A1). However, the polymers and polymer resins used are very expensive and they are not very suitable for processes having a high mass throughput.

SUMMARY OF THE INVENTION

The invention provides a process for separating aluminum chloride from silane liquid, wherein,
in a first step, silane liquid containing aluminum chloride is mixed a with compound N selected from among nitrogen and phosphorus compounds, forming an ionic liquid from the aluminum chloride and compound N,
and, in a second step, the ionic liquid is separated from the purified silane liquid.

DETAILED DESCRIPTION OF THE PREFERRED EMBODIMENTS

It has been found that ionic liquids are virtually insoluble in silanes, in particular in the crude silane. The aluminum chloride reacts with compound N to form an ionic liquid. Two liquid phases are formed here: the phase of the silane liquid and the phase of the ionic liquid.

The silane liquid preferably contains silanes of the general formula 1

$$R_a H_b SiCl_{4-a-b} \qquad (1),$$

where
R is an alkyl radical having from 1 to 6 carbon atoms or a phenyl radical,
a is 0, 1, 2, 3 or 4 and
b is 0, 1 or 2.
R is preferably a methyl radical.

In a preferred embodiment, a is 1, 2 or 3. b is preferably 0 or 1.

In another preferred embodiment, a is 0. b is preferably 1 or 2.

A particularly preferred silane liquid is the silane mixture produced in the Müller-Rochow process, which is referred to as "crude silane."

The silane liquid and/or the compound N can contain solvent, in particular aprotic solvent. The amount of solvent is preferably less than 100% by weight, more preferably not more than 20% by weight, in particular not more than 1% by weight, based on the aluminum chloride-containing silane liquid used.

Examples of solvents are aprotic solvents, preferably linear or cyclic, saturated or unsaturated hydrocarbons, e.g. pentane, cyclohexane, toluene, ethers such as methyl tert-butyl ether, anisole, tetrahydrofuran or dioxane, halogenated hydrocarbons such as dichloromethane, 1,2-dichloroethane or chlorobenzene, nitriles such as acetonitrile or propionitrile, or DMSO.

The aluminum chloride-containing silane liquid used preferably contains not more than 10% by weight, in particular 1% by weight, of solvent. In one embodiment, the aluminum chloride-containing silane liquid used contains chlorinated hydrocarbons. The chlorinated hydrocarbons can be formed as by-products in the Müller-Rochow process.

The compound N is preferably selected from among urea compounds, thiourea compounds, amine compounds, amide compounds, phosphonium salt compounds, pyridine compound and imidazolium salt compounds and mixtures thereof.

As urea compounds, preference is given to urea and alkylated ureas, with at least one hydrogen atom being present on one of the nitrogen atoms.

As thiourea compounds, preference is given to thiourea and alkylated thioureas, with at least one hydrogen atom being present on one of the nitrogen atoms.

As amine compounds, preference is given to primary and secondary amines having C1-C10-alkyl radicals. The amine compounds are preferably liquid or solid under process conditions. Particular preference is given to secondary aliphatic amines.

As amide compounds, preference is given to monomeric carboxamides. The amide compounds are preferably mono-substituted or unsubstituted on the nitrogen atom.

As phosphonium salt compounds, preference is given to phosphonium salts which are tetrasubstituted by C1-C10-alkyl radicals or phenyl radicals. The phosphonium salt compounds are preferably liquid or solid under process conditions.

As pyridine compounds, preference is given to pyridine and N-alkylpyridinium salts having a C1-C10-alkyl radical.

The imidazolium salt compounds are salts of 1,3-diazoles. They are preferably unsubstituted or substituted by a C1-C10-alkyl radical on one or both nitrogen atoms. Particular preference is given to methylimidazolium chloride, 1-ethyl-2-methyl-imidazolium chloride, 1-ethyl-3-methyl-imidazolium chloride and 1-butyl-3-methylimidazolium chloride.

When the compound N is a salt compound, it preferably has the chloride ion as the anion of the salt.

Preference is given to using from 2 to 100, in particular from 5 to 50, parts by weight of compound N per 1 part by weight of aluminum chloride in the silane liquid.

In the first process step, the mixture of aluminum chloride-containing silane liquid with compound N is preferably agitated, in particular stirred.

The first process step is preferably carried out at a pressure of from 500 hPa to 2000 hPa, in particular from 900 hPa to 1200 hPa, and at a temperature of from 0° C. to 50° C., more preferably from 10° C. to 40° C., and in particular from 15° C. to 30° C.

In a preferred embodiment, the phase of the ionic liquid has a greater density than the phase of the silane liquid. In this case, the phases can be separated by draining.

In a further preferred embodiment, the compound N is solid at the process temperature. In this case, the ionic liquid adheres to the unreacted compound N and the phases can be separated by decantation.

All above symbols in the above formulae have their meanings independently of one another. In all formulae, the silicon atom is tetravalent. The sum of all constituents of the reaction mixture is 100% by weight.

In the following examples, all amounts and percentages are by weight and all pressures are 0.10 MPa (abs.), unless indicated otherwise.

Unless indicated otherwise, the examples below were carried out at room temperature, i.e. at 23° C.

Example 1

909.88 g of crude silane are stirred with 68.60 g of urea in a glass flask. After the contact times indicated in Table I, samples of the crude silane phase are taken and the aluminum content of the purified crude silane is determined by means of ICP-AES (inductively coupled plasma-atomic emission spectroscopy, instrument: Optima 7300 DV, Perkin Elmer). The aluminum content of the purified crude silane decreases continually.

TABLE I

Decrease in the aluminum content of the purified crude silane as a function of the contact time during stirring with urea.

| Time [min] | Al [mg/kg] |
| --- | --- |
| 0 | 170 |
| 5 | 97 |
| 10 | 86 |
| 15 | 77 |
| 20 | 63 |
| 25 | 52 |
| 30 | 40 |
| 35 | 32 |
| 40 | 25 |
| 45 | 18 |
| 60 | 10 |
| 75 | 6 |
| 90 | 4 |
| 120 | <3 |

Example 2

200.17 g of crude silane are stirred with 13.03 g of 1-ethyl-2-methylimidazolium chloride in a glass flask. After the contact times indicated in Table II, samples of the crude silane phase are taken and the aluminum content of the purified crude silane is determined by means of ICP-AES (inductively coupled plasma-atomic emission spectroscopy, instrument: Optima 7300 DV, Perkin Elmer). The aluminum content of the purified crude silane decreases continually.

TABLE II

Decrease in the aluminum content of the purified crude silane as a function of the contact time during stirring with 1-ethyl-2-methylimidazolium chloride.

| Time [min] | Al [mg/kg] |
| --- | --- |
| 0 | 160 |
| 5 | 30 |
| 10 | 25 |
| 15 | 22 |
| 20 | 24 |
| 25 | 19 |
| 30 | 20 |
| 35 | 22 |
| 40 | 20 |
| 35 | 16 |
| 60 | 21 |
| 75 | 20 |
| 90 | 16 |
| 120 | 19 |

Example 3

200.14 g of crude silane are stirred with 10.04 g of methylimidazolium chloride in a glass flask. After the contact times indicated in Table III, samples of the crude silane phase are taken and the aluminum content of the purified crude silane is determined by means of ICP-AES (inductively coupled plasma-atomic emission spectroscopy, instrument: Optima 7300 DV, Perkin Elmer). The aluminum content of the purified crude silane decreases continually.

TABLE III

Decrease in the aluminum content of the purified crude silane as a function of the contact time during stirring with methylimidazolium chloride.

| Time [min] | Al [mg/kg] |
| --- | --- |
| 0 | 160 |
| 5 | 27 |
| 10 | 21 |
| 15 | 18 |
| 20 | 19 |
| 25 | 17 |
| 30 | 16 |
| 35 | 16 |
| 40 | 17 |
| 35 | 17 |
| 60 | 17 |
| 75 | 17 |
| 90 | 17 |
| 120 | 18 |

After all experiments, no changes in the composition of the crude silane apart from the decrease in the aluminum content are observed.

The invention claimed is:

1. A process for purifying a silane liquid containing aluminium chloride as a contaminant, comprising the following steps, in the order given:

in a first step, adding at least one compound N selected from the group consisting of urea compounds, thiourea compounds, amine compounds, amide compounds, phosphonium compounds, pyridine compounds and imidazolium salt compounds, to the silane liquid containing aluminium chloride as a contaminant, forming an ionic liquid phase from the aluminum chloride and compound(s) N, and in a second step, separating the ionic liquid from a purified silane liquid which contains a reduced amount of aluminium chloride as compared to the aluminium chloride content of the silane liquid containing aluminium chloride as a contaminant.

2. The process of claim 1, wherein the silane liquid contains silanes of the formula 1

  (1), where

R each independently is an alkyl radical having from 1 to 6 carbon atoms or a phenyl radical, a is 0, 1, 2, 3 or 4 and b is 0, 1 or 2.

3. The process of claim 1, wherein the silane liquid is a crude silane produced in the Müller-Rochow process.

4. The process of claim 2, wherein the silane liquid is a crude silane produced in the Müller-Rochow process.

5. The process of claim 1, wherein the at least one compound N is selected from the group consisting of urea, thiourea, methylimidazolium chloride, and 1-ethyl-2-methylimidazolium chloride.

6. The process of claim 2, wherein the at least one compound N is selected from the group consisting of urea, thiourea, methylimidazolium chloride and 1-ethyl-2-methylimidazolium chloride.

7. The process of claim 3, wherein the at least one compound N is selected from the group consisting of urea, thiourea, methylimidazolium chloride and 1-ethyl-2-methylimidazolium chloride.

8. The process of claim 1, wherein from 2 to 100 parts by weight of compound N are used per 1 part by weight of aluminum chloride in the silane liquid.

9. The process of claim 3, wherein from 2 to 100 parts by weight of compound N are used per 1 part by weight of aluminum chloride in the silane liquid.

10. The process of claim 1, wherein the first process step is carried out at a temperature of from 0° C. to 50° C.

11. The process of claim 3, wherein the first process step is carried out at a temperature of from 0° C. to 50° C.

12. The process of claim 5, wherein the first process step is carried out at a temperature of from 0° C. to 50° C.

13. The process of claim 8, wherein the first process step is carried out at a temperature of from 0° C. to 50° C.

14. The process of claim 1, wherein the first process step is carried out at a temperature of from 0° C. to 30° C.

15. The process of claim 1, wherein the first process step is carried out at a temperature of from 0° C. to 23° C.

16. The process of claim 1, wherein the at least one compound N is selected from the group consisting of urea compounds, thiourea compounds, primary and secondary amines, monomeric carboxamides, pyridine, and mixtures thereof.

17. The process of claim 1, wherein the at least one compound N is selected from the group consisting of urea and thiourea.

18. The process of claim 1, wherein from 5 to 50 parts by weight of compound(s) N are used per 1 part of aluminum chloride in the silane liquid.

19. The process of claim 3, wherein the silane liquid contains chlorinated hydrocarbons from the Müller-Rochow process.

* * * * *